United States Patent
Pavlik (10) Patent No.: US 9,737,863 B2
(45) Date of Patent: Aug. 22, 2017

(54) MIXING ASSEMBLY AND MIXING METHOD

(71) Applicant: ADVANCED SCIENTIFICS, INC., Millersburg, PA (US)

(72) Inventor: Rudolf Pavlik, Millersburg, PA (US)

(73) Assignee: Advanced Scientifics, Inc., Millersburg, PA (US)

(*) Notice: Subject to any disclaimer, the term of this patent is extended or adjusted under 35 U.S.C. 154(b) by 244 days.

(21) Appl. No.: 14/794,641

(22) Filed: Jul. 8, 2015

(65) Prior Publication Data

US 2015/0306554 A1    Oct. 29, 2015

Related U.S. Application Data

(62) Division of application No. 14/338,573, filed on Jul. 23, 2014, now Pat. No. 9,101,893.

(60) Provisional application No. 61/953,987, filed on Mar. 17, 2014.

(51) Int. Cl.
| | |
|---|---|
| *B01F 3/12* | (2006.01) |
| *B01F 11/00* | (2006.01) |
| *B01F 15/00* | (2006.01) |
| *C12M 1/00* | (2006.01) |

(52) U.S. Cl.
CPC ........ *B01F 15/0085* (2013.01); *B01F 3/1221* (2013.01); *B01F 11/0082* (2013.01); *B01F 15/00129* (2013.01); *B01F 15/00155* (2013.01); *B01F 15/00207* (2013.01); *B01F 15/00253* (2013.01); *B01F 15/00259* (2013.01); *B01F 15/00402* (2013.01); *B01F 15/00538* (2013.01); *C12M 23/14* (2013.01);
(Continued)

(58) Field of Classification Search
CPC .............. B01F 11/0048; B01F 11/0082; B01F 15/00129; B01F 15/00155; B01F 15/00207; B01F 15/00253; B01F 15/00259; B01F 15/00402; B01F 15/00467; B01F 15/00538; B01F 15/0085; B01F 2215/0073; B01F 3/1221
USPC ................................ 366/332, 142, 203, 205
See application file for complete search history.

(56) References Cited

U.S. PATENT DOCUMENTS

| | | |
|---|---|---|
| 1,776,405 A | 9/1930 | Wilsey |
| 2,513,577 A | 7/1950 | Malme |
| 2,631,091 A | 3/1953 | Kuentzel et al. |
| (Continued) | | |

OTHER PUBLICATIONS

International Search Report and Written Opinion dated Jun. 17, 2015, issued in PCT Application No. PCT/US2015/020665, filed Mar. 16, 2015.

*Primary Examiner* — Tony G Soohoo
(74) *Attorney, Agent, or Firm* — Workman Nydegger (57) ABSTRACT

A mixing system and mixing method are provided. The mixing system includes a tank assembly, a container positioned within the tank assembly, a mixer disposed within a compartment of the container, a linear motor, and a shaft having a first end secured to the mixer and an opposing second end secured to the linear motor. The linear motor provides a variable stroke length for the shaft. The mixing method includes providing a tank assembly having a linear motor, positioning a mixing assembly including a mixing bag in the tank assembly, combining two or more components in a compartment of the mixing bag, attaching a mixing shaft extending from a mixer disposed within the mixing bag to the linear motor, and raising and lowering the mixing shaft to mix the two or more components. A stroke length of the mixing shaft during the raising and lowering is varied.

16 Claims, 8 Drawing Sheets

(52) U.S. Cl.
CPC ..... *B01F 11/0048* (2013.01); *B01F 15/00467* (2013.01); *B01F 2215/0073* (2013.01)

(56) References Cited

U.S. PATENT DOCUMENTS

| | | | |
|---|---|---|---|
| 2,661,938 A | 12/1953 | Kuentzel | |
| 2,780,444 A | 2/1957 | Hickey | |
| 2,892,620 A | 6/1959 | Derrick | |
| 3,206,172 A | 9/1965 | Brejcha et al. | |
| 3,945,618 A | 3/1976 | Shoh | |
| 4,195,981 A | 4/1980 | Penberthy | |
| 4,423,945 A | 1/1984 | Preston et al. | |
| 4,511,254 A | 4/1985 | North et al. | |
| 4,605,172 A | 8/1986 | Ahlert | |
| 4,732,487 A | 3/1988 | Pollard | |
| 4,907,723 A | 3/1990 | Katz | |
| 4,907,891 A | 3/1990 | Pointon | |
| 5,879,081 A | 3/1999 | Chordia | |
| 6,416,215 B1 | 7/2002 | Terentiev | |
| 6,491,422 B1 | 12/2002 | Rutten et al. | |
| 6,494,613 B2 | 12/2002 | Terentiev | |
| 6,889,454 B2 | 5/2005 | Chandaria | |
| 6,908,223 B2 | 6/2005 | Bibbo et al. | |
| 6,923,567 B2 | 8/2005 | Bibbo et al. | |
| 6,965,288 B2 | 11/2005 | Terentiev | |
| 6,981,794 B2 | 1/2006 | Bibbo et al. | |
| 7,086,778 B2 | 8/2006 | Terentiev | |
| 7,267,479 B2 | 9/2007 | Terentiev | |
| 7,357,567 B2 | 4/2008 | Terentiev | |
| 7,384,027 B2 | 6/2008 | Terentiev et al. | |
| 7,434,983 B2 | 10/2008 | Terentiev | |
| 7,469,884 B2 | 12/2008 | Terentiev et al. | |
| 7,481,572 B2 | 1/2009 | Terentiev | |
| 7,516,648 B2 | 4/2009 | Terentiev | |
| 7,695,186 B2 | 4/2010 | Terentiev | |
| 7,762,716 B2 | 7/2010 | Terentiev et al. | |
| 7,992,846 B2 | 8/2011 | Terentiev et al. | |
| 8,123,188 B2 | 2/2012 | Banfield | |
| 8,905,624 B1 | 12/2014 | Howe et al. | |
| 8,979,357 B1 | 3/2015 | Pavlik | |
| 2005/0249033 A1 | 11/2005 | Krause | |
| 2009/0245015 A1 | 10/2009 | Ni et al. | |
| 2010/0197003 A1 | 8/2010 | Terentiev et al. | |

MIXING ASSEMBLY AND MIXING METHOD

CROSS-REFERENCE TO RELATED APPLICATIONS

This application is a divisional of U.S. application Ser. No. 14/338,573, filed Jul. 23, 2014, now U.S. Pat. No. 9,101,893, which claims the benefit of and priority to U.S. Provisional Patent Application No. 61/953,987 filed Mar. 17, 2014, which are hereby incorporated by reference in their entirety.

FIELD OF THE INVENTION

The present invention is directed to a mixing assembly and mixing method. More specifically, the present invention is directed to a mixing assembly having a variable stroke distance, and a mixing method including a variable stroke distance.

BACKGROUND OF THE INVENTION

Culture media, buffers, reagents and other biological materials (hereinafter "base materials") are used extensively by biotech companies in research and development, creating vaccines, producing and purifying proteins, and developing other biologicals. Many base materials include precise compositions and are often highly regulated. Additionally, to be safe and effective for their intended use, these base materials must be pure and sterile. As such, the manufacture of base materials is expensive and often requires specialized equipment.

Due to the huge expense of creating, operating, and maintaining the elaborate systems used in the manufacture of base materials, biotech companies frequently purchase the base materials in their final solution form. However, in the solution form, the base materials often consist primarily of water, and as such, can be difficult and expensive to transport. Additionally, the final liquid solutions frequently have a significantly shorter shelf life as compared to powdered base materials, and must typically be stored under refrigerated conditions, which increases the storage cost.

To decrease costs, the base materials may be shipped and/or stored in their powdered form and mixed later. During the initial mixing with the liquid, the powdered base materials are usually concentrated or settled at the bottom of the mixing container. When concentrated or settled at the bottom the powdered base materials may be difficult to break up, and can damage the mixing device. One method of breaking up the concentrated powdered base materials includes shaking the entire mixing container. However, shaking the mixing container creates a risk for disposable tank liners, and also presents limitations on the size of the mixing container.

A mixing assembly and mixing method that show one or more improvements in comparison to the prior art would be desirable in the art.

BRIEF DESCRIPTION OF THE INVENTION

In an embodiment, a mixing system includes a tank assembly, a container positioned within the tank assembly, a mixer disposed within a compartment of the container, a linear motor, and a shaft having a first end secured to the mixer and an opposing second end secured to the linear motor. The linear motor provides a variable stroke length for the shaft.

In another embodiment, a mixing system includes a tank assembly including a side wall and a floor defining a chamber, a container positioned within the chamber, a mixer disposed within a compartment of the container, a servo motor, a shaft having a first end secured to the mixer and an opposing second end extending from the container and secured to the servo motor, and a sensor to measure a thickness of a settlement within the container. A stroke length of the servo motor is configured to vary in length in response to measurements from the sensor.

In another embodiment, a mixing method includes providing a tank assembly having a linear motor; positioning a mixing assembly in the tank assembly, the mixing assembly including a mixing bag, a mixer disposed within the mixing bag, and a mixing shaft attached to the mixer and extending from the mixing bag; combining two or more components in a compartment of the mixing bag; attaching the mixing shaft to the linear motor; and raising and lowering the mixing shaft to mix the two or more components. A stroke length of the mixing shaft during the raising and lowering is varied.

An advantage of the mixing assembly, according to the embodiments disclosed herein, includes decreasing stress on the mixing assembly when settlements are present on the bottom of a mixing tank.

Another advantage includes increasing efficiency of the mixing assembly.

Further advantages include increasing a lifespan of the mixing assembly, decreasing risk to disposable tank liners, decreasing limitations on the size of the mixing container, and combinations thereof.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
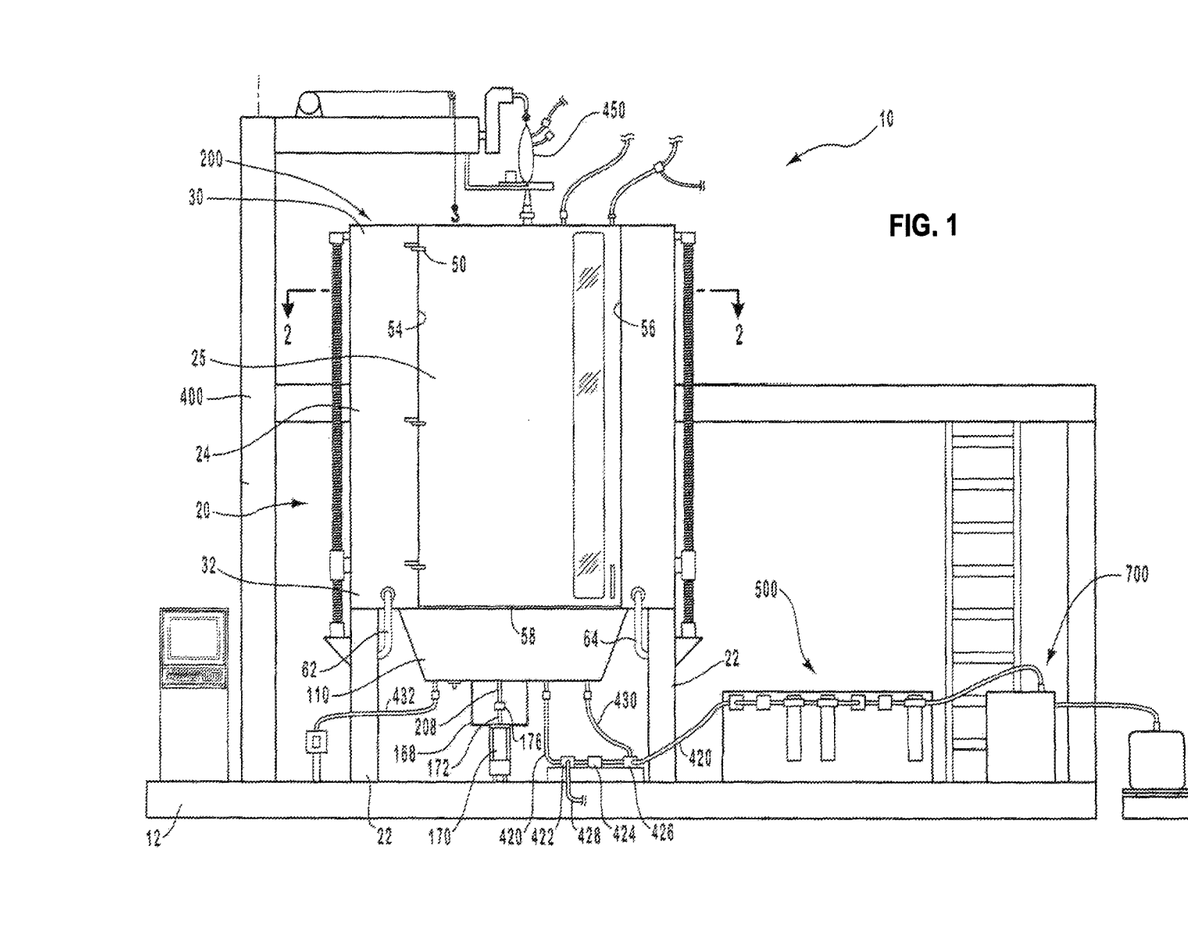
FIG. 1 is a perspective view of a mixing system.

Referring to FIG. 1, in one embodiment, a mixing system 10, such as, but not limited to, an imPULSE Mixing System available from Advanced Scientifics Incorporated in Millersburg, Pa., is provided for mixing two or more components, at least one of the components being liquid, so as to produce a homogenous solution. In addition to at least one of the components being liquid, other components of the two or more components include, but are not limited to, liquids, gels, dry materials, or combinations thereof. For example, in one embodiment, each of the two or more components is liquid. In an alternate embodiment, one of the two or more components is a liquid, such as water, and another component is a dry or substantially dry material, such as powder, grain, granule, or other form of solid.

The mixing system 10 is used to produce any suitable form of solution, such as, but not limited to a sterile solution or a non-sterile solution. Suitable solutions include, for example, culture media, buffers, reagents, and other biological materials that may or may not be sterile. In one embodiment, the two or more components are combined in the mixing system 10 and mixed to form the solution. In another embodiment, the mixing system 10 is used to produce a homogenous or substantially homogenous solution from a solution that has settled, such as, for example, a stored solution. In a further embodiment, the mixing system 10 is adjustable based upon a settling of the solution.

In one embodiment, the mixing system 10 includes at least one disposable component, such as a structural component that directly contacts the solution during manufacture. In another embodiment, any of the structural components contaminated by contact with the solution are replaced with new components prior to the manufacture of different batches and/or types of solutions. Based upon the type of solution, the new components are either sterile or non-sterile. The use of the disposable components reduces manufacturing time, down time, and/or expense by reducing or eliminating sterilization or cleaning of the mixing system 10. Alternatively, some or all of the components are designed for sterilization and reuse.

In one embodiment, the mixing system 10 includes at least one tank assembly 20 mounted on a platform 12, a mixing assembly 200 at least partially disposed within the tank assembly 20, an actuation mechanism 170 detachably secured to the mixing assembly 200, and a filtration system 500 in fluid communication with the mixing assembly 200. In another embodiment, the platform 12 is a movable platform, on which some or all of the components of the mixing system 10 are mounted. In a further embodiment, the mixing system 10 is formed as a modular unit to provide portability and ease of assembly. Alternatively, the mixing assembly 200 is permanently assembled on site without the platform 12.

Figure 2:
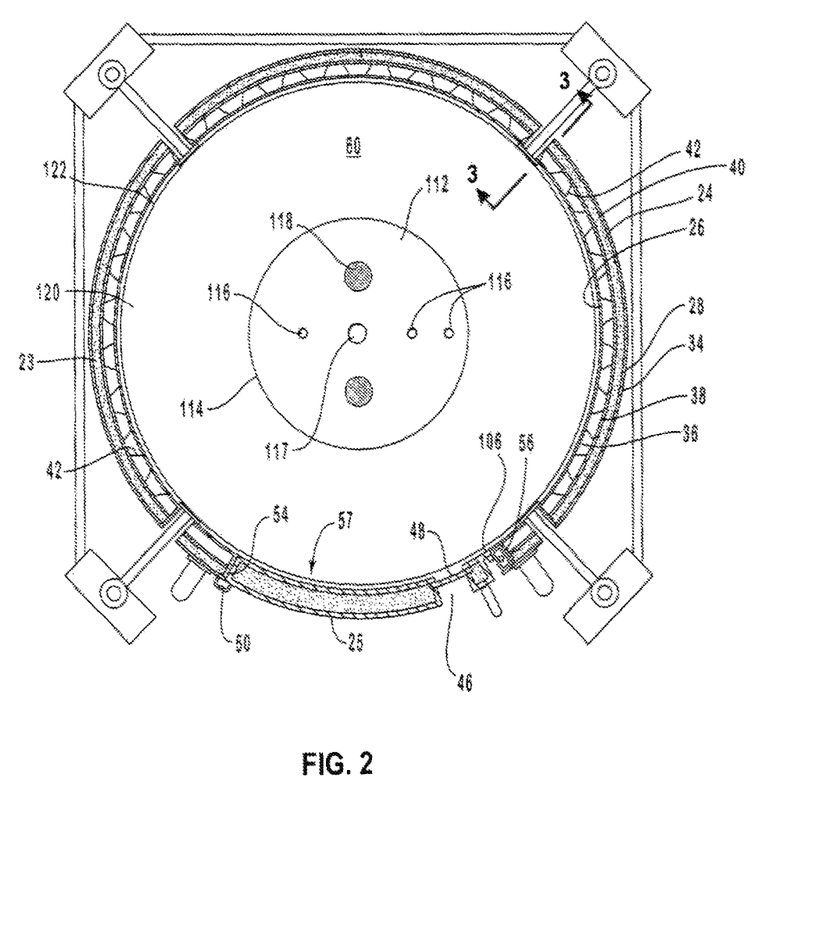
FIG. 2 is a top view of a tank assembly.

The at least one tank assembly 20 includes any suitable number of tank assemblies having the same or different sizes, shapes, and/or properties, each of the at least one tank assemblies 20 being mounted on or off of the platform 12. In one embodiment, the tank assembly 20 includes a plurality of legs 22 upstanding from the platform 12 and supporting an annular side wall 24. As illustrated in FIGS. 1 and 2, in one embodiment, the side wall 24 has an interior surface 26 and an exterior surface 28 each extending between an upper end 30 and an opposing lower end 32. The interior surface 26 at least partially bounds a chamber 60. The side wall 24 has a tubular configuration so that the upper end 30 and the lower end 32 are open.

In another embodiment, the side wall 24 includes a body portion 23 having a substantially C-shaped transverse cross section. Other transverse cross section shapes include, but are not limited to, circular, polygonal, or hexagonal. In another embodiment, the polygonal transverse cross section shape increases turbulent flow to provide increased mixing of the two or more components. The body portion 23 terminates at substantially opposing end plates 54 and 56 with a doorway 57 formed therebetween. In one embodiment, to increase a hoop strength of the body portion 23, a support brace 58 rigidly extends between the end plates 54 and 56 at the lower end 32. In a further embodiment, the body portion 23 includes an outer wall 34, a concentrically disposed inner wall 36 and a central wall 38 concentrically disposed between the outer wall 34 and the inner wall 36. The outer wall 34, the inner wall 36 and the central wall 38 each connect with the end plates 54 and 56, as well as extend between and rigidly connect with a top plate 70 and an opposing bottom plate 72.

Disposed between the outer wall 34 and the central wall 38 is an insulation layer 40. In one embodiment, the insulation layer 40 includes an insulating material, such as, but not limited to, a chloride free, ceramic fiber capable of withstanding temperatures of up to at least 1,300° C. In another embodiment, a door 25 is disposed within a doorway 57 between the end plates 54 and 56. In a further embodiment, the door 25 includes the outer wall 34, the inner wall 36, and the layer of insulation 40 disposed therebetween. Hinges 50 secure the door 25 to the body portion 23 to permit opening of the door 25, thus providing access to the chamber 60. In one embodiment, a viewing window 48 disposed in a viewing slot 46 on the door 25 provides an unobstructed view of the chamber 60 when the door 25 is closed. The door 25 is locked in a closed position by any suitable locking means, such as, but not limited to, locking flanges 106 and stops, dead bolts, other interlocking members, or a combination thereof.

Extending between the central wall 38 and the inner wall 36 of the body portion 23 and/or the door 25 are a plurality of spaced apart spacers 42. The spacers 42 include, for example, discrete members or formations projecting from the central wall 38 and/or the inner wall 36. The spacers 42 provide structural stability for both the central wall 38 and the inner wall 36, while permitting fluid to flow between the central wall 38 and the inner wall 36, and around the spacers 42. The fluid flowing between the central wall 38 and the inner wall 36 may be heated or cooled to heat or cool a solution held within the chamber 60 of the tank assembly 20. Additionally, the mixing system 10 may include a temperature probe for continuously measuring the temperature of the solution within the mixing bag 202. For example, in one embodiment, the temperature probe continuously measures the surface temperature of the mixing bag 202 to determine the temperature of the solution therein.

A floor 112 of the tank assembly 20 provides support for the mixing assembly 200 when positioned thereon. A plurality of open port holes 116 and/or a central port hole 117 extend through the floor 112. In one embodiment, a plurality of screened spill holes 118 is formed on the floor 112. The floor 112 is circular, polygonal, elliptical, irregular, flat, substantially flat, frustoconical, curved, pyramidal, conical, any other configuration for supporting a bag, or a combination thereof. For example, in one embodiment, the floor 112 includes a flat or substantially flat portion 114, which is circular, and a peripheral wall 120 that slopes upwardly and outwardly from the flat or substantially flat portion 114 to a terminal edge 122. Outwardly projecting from the terminal edge 122 is a lip 124 that is either biased directly against or terminates directly adjacent to the interior surface 26 of the side wall 24. In another embodiment, the floor 112 and the side wall 24 are made of a metal, such as, for example, stainless steel. In a further embodiment, the lip 124 is polypropylene, rubber, silicone, moldable plastic, any other resilient material, or a combination thereof.

Figure 3A:
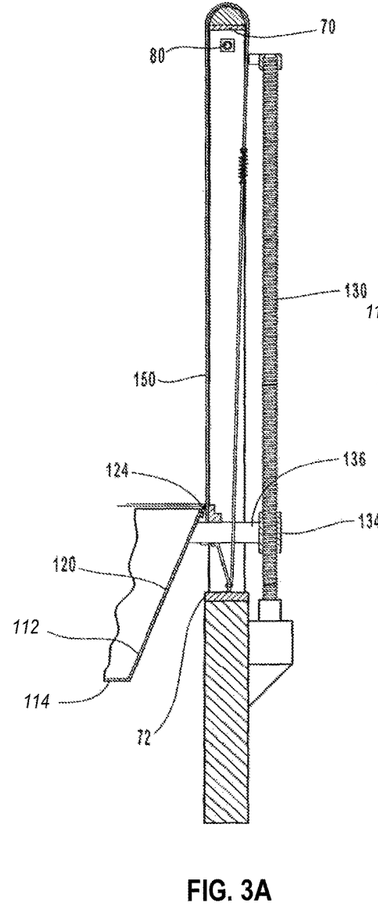
FIG. 3A is a cross-sectional view of an adjustable floor in a lowered position within a tank assembly according to an embodiment of the disclosure.
Figure 3B:
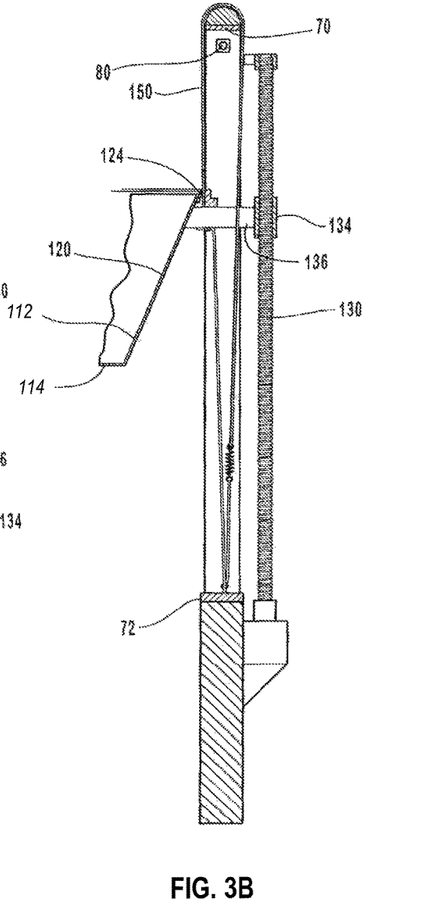
FIG. 3B is a cross-sectional view of an adjustable floor in a raised position within a tank assembly according to an embodiment of the disclosure.

In one embodiment, as illustrated in FIGS. 2-3B, the floor 112 is an adjustable floor having a strut 136 extending between the peripheral wall 120 and a collar 134. A level of the adjustable floor is raised or lowered relative to the side wall 24. In another embodiment, the adjustable floor is raised or lowered, for example, by simultaneous rotating one or more threaded members 130 positioned outside of the side wall 24. The rotating of the one or more threaded members 130 raises or lowers one or more of the collars 134 engaged therewith to raise or lower the floor 112. Alternate embodiments include, but are not limited to, raising or lowering the adjustable floor with chain drives, belt drives, gear drives, hydraulic lifts, pneumatic lifts, jacks, cranks, winches, pulley systems, any other suitable mechanism for raising or lowering struts 136 extending from the exterior surface 28 of side wall 24, or a combination thereof. The raising or lowering of the adjustable floor relative to the side wall 24 adjusts a size of the chamber 60 bound by the side wall 24 and the floor 112. For example, raising the adjustable floor decreases the size of the chamber 60, while lowering the adjustable floor increases the size of the chamber 60. In an alternate embodiment, the floor 112 is fixed and does not raise or lower, thus fixing the size of the chamber 60. The size of the chamber 60 includes, but is not limited to, 5 liters, 20 liters, 250 liters, 500 liters, 750 liters, 1,000 liters, 1,500 liters, 3,000 liters, 5,000 liters, 10,000 liters, or any other suitable size.

Figure 4:
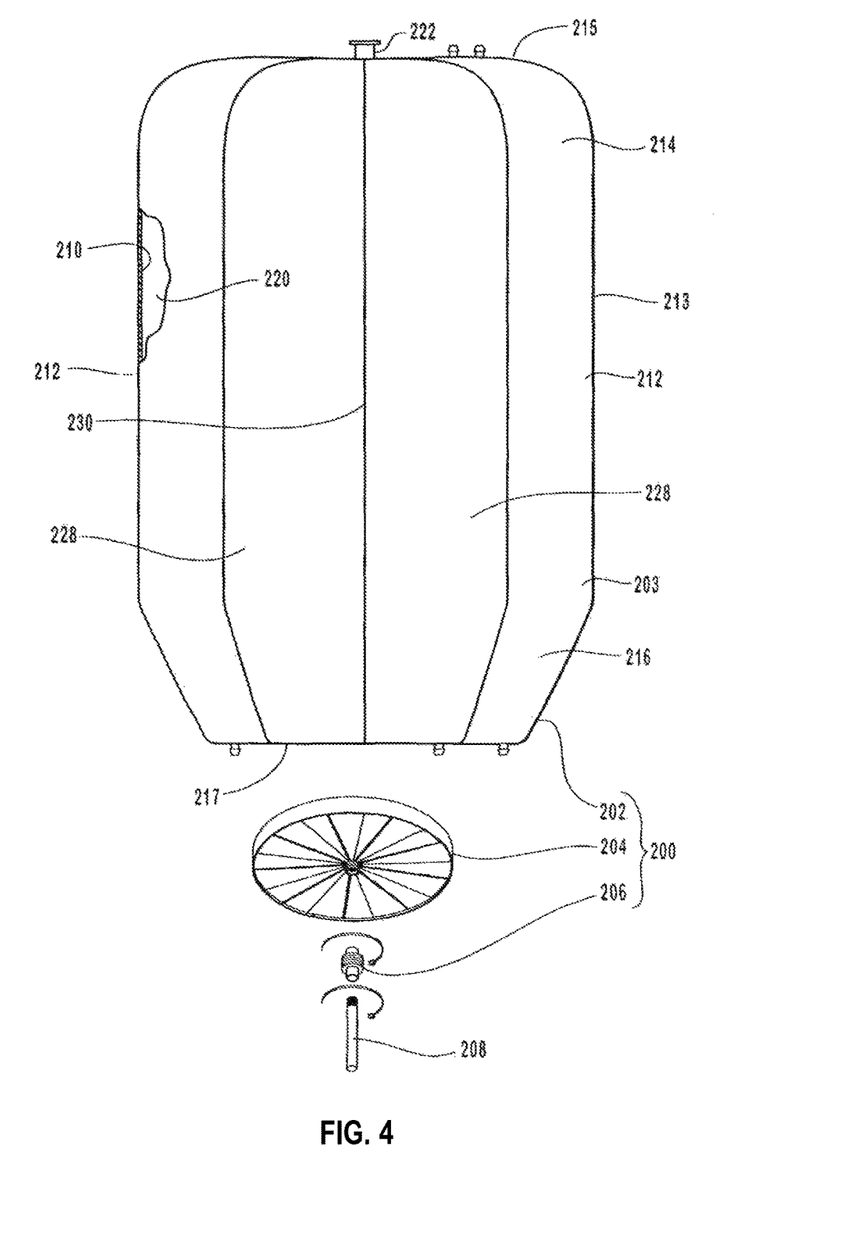
FIG. 4 is an exploded perspective view of a mixing bag assembly.

Referring to FIG. 4, in one embodiment, the mixing assembly 200 includes a mixing bag 202, such as, but not limited to, those sold by Advanced Scientifics Incorporated of Millersburg, Pa., for use in combination with its imPULSE Mixing System. In another embodiment, the mixing assembly 200 includes a mixer 204, an expandable tubular seal 206, and/or a mixing shaft 208. The mixing bag 202 provides a compartment 220 for containing the solution therein prior to, during, and/or after the mixing of the two or more components. For example, in one embodiment, the mixing bag 202 includes an elongated body 203 having an exterior surface 212 and an interior surface 210 that bounds the compartment 220. In another embodiment, the mixing bag 202 includes any suitable combination of plies, materials, thicknesses, panels 228, and/or seams 230 for containing the solution therein, as described in U.S. Pat. No. 6,923,567, which issued on Aug. 2, 2005, and is hereby incorporated by specific reference. For example, the body 203 of one mixing bag includes a flexible, water impermeable, single ply material having a thickness of between about 0.1 mm to about 5 mm, and being formed from three or more of the panels 228.

The body 203 and/or the compartment 220 of the mixing bag 202 include any shape, size, and/or configuration for being positioned within the chamber 60 of the mixing system 10. For example, in one embodiment, the body 203 includes a side wall 213 that, when the body 203 is inflated or filled, has a substantially circular or rounded polygonal transverse cross section extending between an upper end 214 and an opposing lower end 216. The upper end 214 terminates at a top end wall 215 while the opposing lower end 216 terminates at a bottom end wall 217. In another embodiment, the body 203 bounds the compartment 220 sized to hold fluid amounts, such as, but not limited to, 5 liters, 20 liters, 250 liters, 500 liters, 750 liters, 1,000 liters, 1,500 liters, 3,000 liters, 5,000 liters, 10,000 liters, or any other suitable amount.

Figures 5, 6:
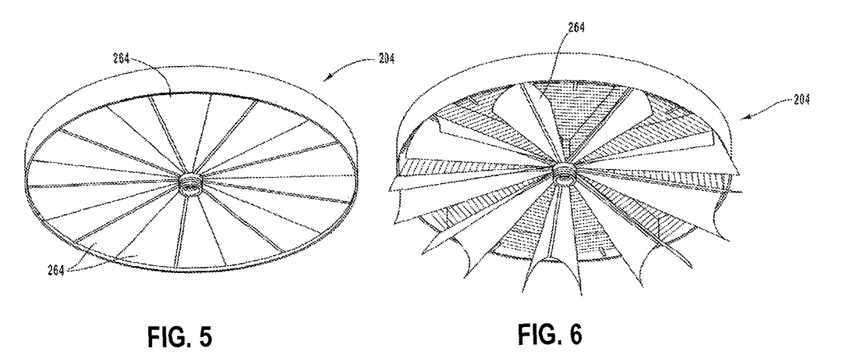
FIG. 5 is a bottom perspective view of a mixer according to an embodiment of the disclosure.
FIG. 6 is a bottom perspective view of the mixer shown in FIG. 10 with the flaps thereof being downwardly flexed.

Referring to FIGS. 5-6, the mixer 204 includes any article for providing agitation and/or swirling of the solution within the mixing bag 202. For example, in one embodiment, the mixer 204 includes a base 205 having a threaded recess 252 for receiving the mixing shaft 208 therein. In another embodiment, the base 205 includes flaps 264 movably mounted thereon. The flaps 264 pivoting, for example, to provide mixing when moved in one direction and fluid flow through the base 205 when moved in an opposite direction. Other embodiments of the mixer 204 include, but are not limited to, those disclosed in U.S. Pat. No. 6,923,567.

Figure 7:
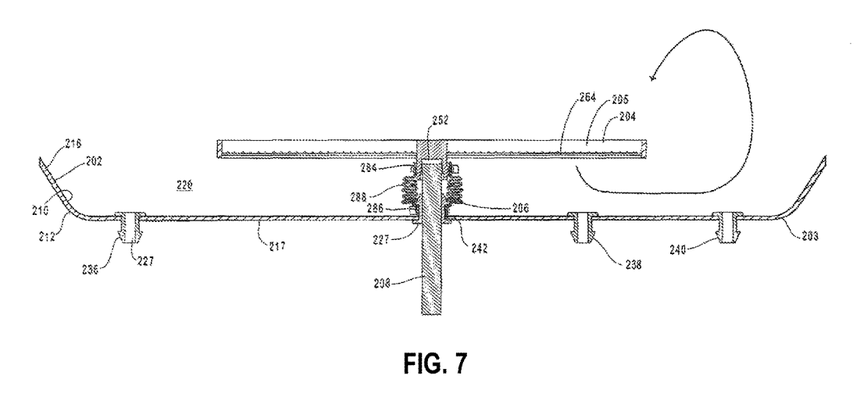
FIG. 7 is a cross-sectional view of a bottom end of a mixing bag having a mixer disposed therein.

Referring to FIG. 7, the mixing shaft 208 includes a first end for being secured to a threaded recess 252 of the mixer 204 within the mixing bag 202, and an opposing second end for extending through the body 203 of the mixing bag 202. For example, the second end of the mixing shaft 208 extends through the top end wall 215, the bottom end wall 217, or any other portion of the body 203. In one embodiment, the mixing shaft 208 is integral with the mixer 204 and forms a portion of the mixing assembly 200. Alternatively, the mixing shaft 208 is detachably secured to the mixer 204 to form a separate component from the mixing assembly 200. In one embodiment, more than one of the mixers 204 is secured to the mixing shaft 208.

In one embodiment, the mixing shaft 208 extends through the expandable tubular seal 206, which is positioned over a mounting port 242 on the top end wall 215 or the bottom end wall 217. The tubular seal 206 includes, but is not limited to, a first end 284, an opposing second end 286, and an expandable bellow section 288 extending therebetween. When the mixing shaft 208 moves relative to the mixing bag 202, the bellow section 288 selectively expands and contracts to maintain a seal communication between the mixer 204 and the mounting port 242. By maintaining the seal communication between the mixer 204 and the mounting port 242, the expandable tubular seal 206 provides a fluid sealed connection between the mixing bag 202 and the mixer 204 to prevent leaking of the solution from the compartment 220 during mixing. Other arrangements are also possible to prevent leaking of the solution from the compartment 220.

Figure 8:
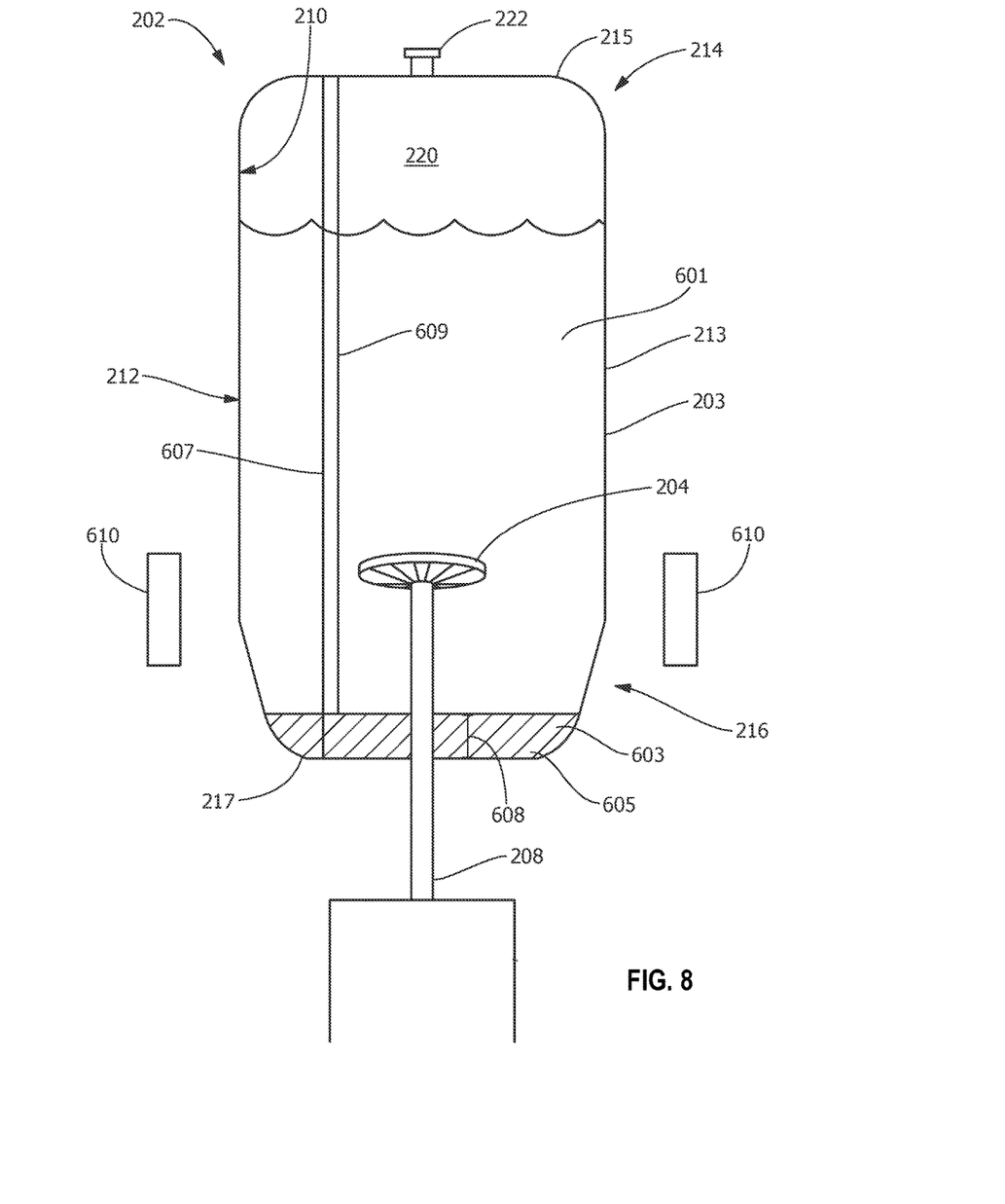
FIG. 8 is a partial cross-sectional view of a mixing assembly having a solution disposed therein.

Referring to FIGS. 1 and 8, an actuation mechanism 170 is provided to move the mixer 204 attached to the mixing shaft 208 in a reciprocating fashion (i.e., axial). The actuation mechanism 170 is detachably secured to the second end of the mixing shaft 208 either directly or through one or more connecting portions. For example, in one embodiment, the actuation mechanism 170 operates an actuation rod 172, which is detachably secured to the mixing shaft 208 through a coupler 176. The actuation mechanism 170 is positioned in any suitable position relative to the tank assembly 20 and/or the mixing assembly 200, based upon an orientation of the mixing assembly 200 in the chamber 60. Suitable positions of the actuation mechanism 170 include, for example, mounted on or adjacent to the upper end 30 or the lower end 32, or along the side wall 24 of the tank assembly 20. In one embodiment, when the mixing shaft 208 extends through the bottom end wall 217 and/or the central port hole 117 of the floor 112, the actuation mechanism 170 is mounted to a frame 168 that is secured to and extends below the floor 112. When mounted to the frame 168, the actuation mechanism raises and lowers with the floor 112. In an alternate embodiment, the actuation mechanism 170 is mounted on the platform 12 or a ground surface, such as, for example, when the floor 112 is fixed in the tank assembly 20. In one embodiment, when the mixing shaft 208 extends through the top end wall 215 the actuation mechanism 170 is mounted and/or positioned adjacent to the upper end 30. For example, in another embodiment, the actuation mechanism 170 is mounted on a lift 400. To provide horizontal reciprocation of the mixing shaft 208, the actuation mechanism 170 is positioned in any suitable location along the side wall 24.

The actuation mechanism 170 includes any mechanism for varying a stroke length of the mixing shaft 208. For example, in one embodiment, the actuation mechanism 170 includes a linear motor, such as, but not limited to, a servo motor, a linear actuator, air cylinders, any other motor capable of a rapid change in direction, or a combination thereof. Preferably, a servo motor is employed that can provide an infinitely and continuously variable stroke length. In another embodiment, the actuation mechanism 170 varies the stroke length of the mixing shaft 208 during mixing of the solution within the mixing bag 202. For example, variation of the stroke length includes, but is not limited to, continuous, stepwise, pre-determined, measured, or a combination thereof.

Figure 9:
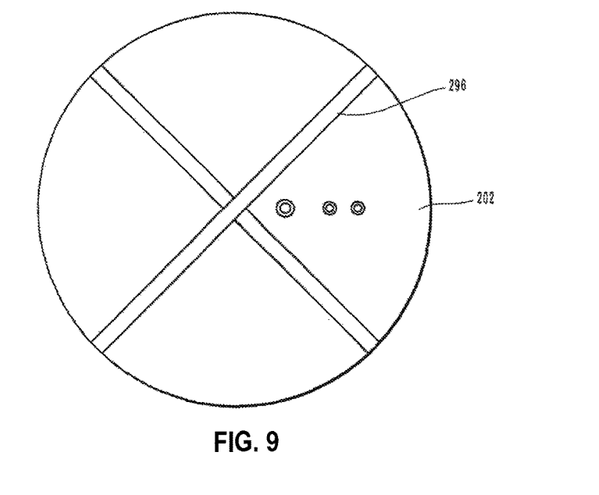
FIG. 9 is a top view of a mixing bag.

In one embodiment, a method 300 of mixing the solution includes positioning the mixing assembly 200 in the tank assembly 20 (step 301), combining the two or more components in the compartment 220 of the mixing bag 202 (step 303), and mixing the two or more components with the actuation mechanism 170 to form the solution (step 305). The positioning of the mixing assembly 200 in the tank assembly 20 (step 301) includes inserting the mixing bag 202 within the chamber 60. In one embodiment, prior to inserting the mixing bag 202 within the chamber 60, the floor 112 is raised or lowered to adjust the size of the chamber 60 based upon an amount of solution to be manufactured. In another embodiment, inserting the mixing bag 202 within the chamber 60 includes, for example, connecting the lift 400 to a harness 296 (FIG. 9) secured to the body 203 of the mixing assembly 200, raising the mixing assembly 200 with the lift 400, guiding the mixing assembly 200 through the doorway 57, and lowering the bottom end wall 217 of the mixing assembly 200 onto the floor 112 within the chamber 60. In an alternate embodiment, the mixing bag 202 is manually inserted into the chamber 60 of the tank assembly 20.

During the lowering of the bottom end wall 217 onto the floor 112, the features extending from the bottom end wall 217 are aligned with the port holes 116 in the floor 112. When the mixing shaft 208 extends from the bottom end wall 217, the mixing shaft 208 is aligned with and passed through the central port hole 117 in the floor 112 during the lowering of the bottom end wall 217 onto the floor 112. After inserting the mixing bag 202 with the chamber 60 the mixing shaft 208 is coupled to the actuation mechanism 170. When the mixing shaft 208 extends from the top end wall 215, the mixing shaft 208 is coupled to the actuation mechanism 170 at any time after the mixing assembly 200 is detachably secured to the lift 400.

Figure 10:
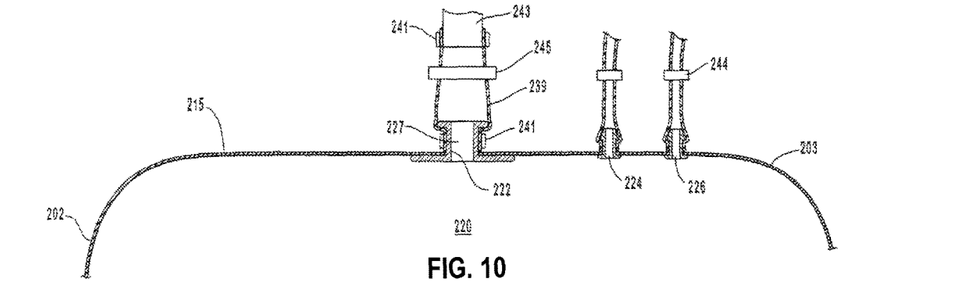
FIG. 10 is a cross-sectional view of a top end of a mixing bag.
Figure 11:
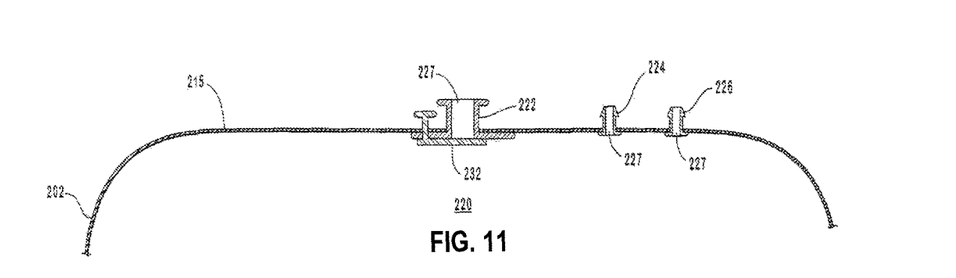
FIG. 11 is a cross-sectional view of a top end of a mixing bag including a cover plate according to an embodiment of the disclosure.

Next, one or more tubes are coupled to features extending from the bottom end wall 217 and/or the top end wall 215 of the mixing assembly 200. Referring to FIGS. 7 and 10-11, in one embodiment, the features extending through the top end wall 215 and/or the bottom end wall 217 of the mixing bag 202 provide fluid communication between the compartment 220 and the exterior. For example, referring to FIG. 7, in another embodiment, an inflation portion 236, an outlet port 238, an inlet port 240, and a mounting port 242 are mounted on the bottom end wall 217, each having a channel 227 extending therethrough to provide the fluid communication. Referring to FIGS. 10-11, in a further embodiment, the mixing bag 202 includes a feeding port 222, a fluid port 224, and a pressure port 226 mounted on the top end wall 215 of the body 203, each having the channel 227 extending therethrough. The channel 227 of each port mounted on either the top end wall 215 or the bottom end wall 217 is closed by any suitable sealing member, such as, but not limited to, an extension sleeve 239, a removable clamp 245, a tie 241, a cover plate 232, or a combination thereof.

The plurality of features, alone or in combination, facilitate filling, draining, and/or mixing of the solution within the compartment 220. In one embodiment, the feeding port 22, the fluid port 224, the pressure port 226, the inflation port 236, the outlet port 238, and/or the inlet port may facilitate filling and/or draining of the solution, while the mounting port 242 receives the mixing shaft 208 therethrough to facilitate mixing of the solution with the mixer 204. For example, in another embodiment, a delivery tube 420 is coupled with the outlet port 238, the delivery tube 420 passing through or coupling with a first valve 422, a pump 424, a second valve 426, and a filtration system 500. In another example, a sample tube 428 is coupled with the first valve 422, and a return tube 430 extends between the second valve 426 and the inlet port 240. In one embodiment, an air tube 432 is coupled with the inflation port 236 and a gas source. The gas source provides compressed gas, such as air, through the inlet port 240 to inflate the mixing bag 202. Once the mixing bag 202 is inflated, a fluid line 440 is coupled with the fluid port 224. Alternatively, the fluid line 440 is coupled to the fluid port 224 without coupling the air tube 432 to the inflation port 236 and/or inflating the mixing bag 202.

During the inflating of the mixing bag 202, the providing the components, and/or the dispensing of the solution, a pressure regulator 442 (FIG. 12) selectively controls a pressure within the mixing bag 202. The pressure regulator 442 is coupled with the pressure port 226 and includes an air inlet line 444 and an air outlet line 446. The air inlet line is coupled to a pump or pressurized gas source to deliver air or other gases into the mixing bag 202, and the air outlet line 446 to permit gas to escape from the mixing bag 202 while maintaining a feed component 603 within the mixing bag 202.

Figure 12:
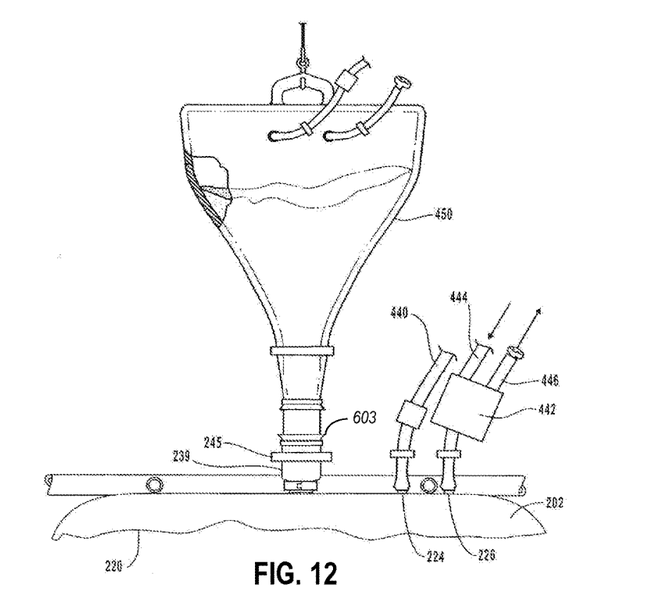
FIG. 12 is a side view of a feed bag coupled with a top end of a mixing bag.
Figure 13:
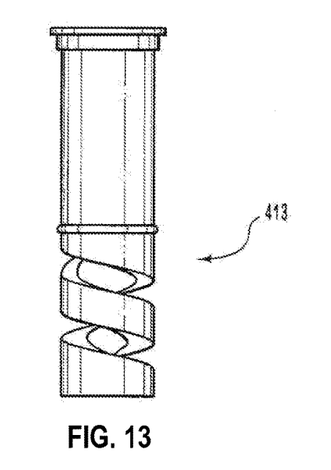
FIG. 13 is a side view of a spray nozzle.
Figure 14:
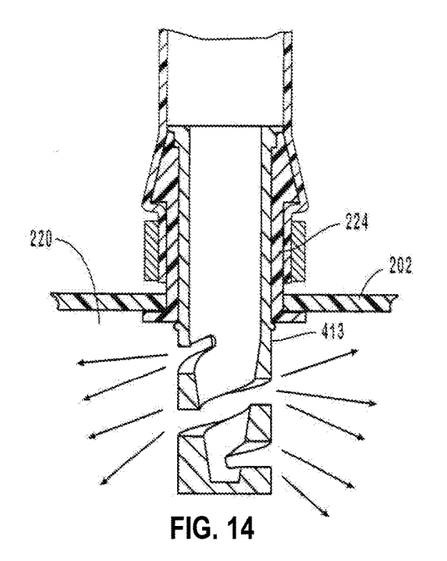
FIG. 14 is a cross-sectional view of a spray nozzle disposed within a port of a mixing bag.

Referring to FIG. 12, subsequent to inserting the mixing bag 202, the combining of the two or more components (step 303) includes providing at least one of the two or more components to the compartment 220. For example, in one embodiment, at least a portion of a fluid component 601, such as water, is selectively dispensed into the compartment 220 through the fluid line 440 coupled to the fluid port 224. In another embodiment, the feed component 603, such as, but not limited to, the dry or substantially dry material (e.g., culture media, buffers, or reagents in a powder form) is dispensed into the compartment 220 from a feed bag 450 coupled to the feeding port 222. The fluid component and the feed component 603 are dispensed separately and/or concurrently into the compartment 220. Referring to FIGS. 13-14, in one embodiment, the fluid component is dispensed through a spray nozzle 413 removably mounted to the fluid port 224. The spray nozzle 413 provides a radial outward spraying of the fluid component 601 to facilitate movement of feed component particles that may have collected the side walls of the mixing bag 202 and submersion of the feed component particles that may be suspended or floating within the mixing bag 202.

During and/or subsequent to the providing at least one of the two or more component to the compartment 220, the actuation mechanism 170 is activated to move the mixer 204 in a reciprocating fashion. The raising and lowering of the mixer 204 mixes the components to generate a homogenous solution. In an alternate embodiment, the feed component 603 and/or the fluid component 601 are stored in the mixing bag 202 prior to the positioning of the mixing assembly 200 or the activation of the actuation mechanism 170. In another embodiment, during the storing of the feed component 603 and/or the fluid component 601, one or more particulates settle in the mixing bag 202 to form a settlement 605 at the bottom of the compartment 220. The one or more particulates include, but are not limited to, the feed component 603.

In one embodiment, the stroke length and/or speed provided by the actuation mechanism 170 is varied to reduce or eliminate stress on the mixer 204, the mixing shaft 208, and/or the actuation mechanism 170, from the mixer 204 contacting the settlement 605. For example, in another embodiment, the stroke length is reduced from a full stroke length 607 to a reduced stroke length 609 by a distance equal to a thickness 608 of the settlement 605. When the actuation mechanism 170 is mounted and/or positioned adjacent to the upper end 30, reducing the stroke length includes reducing the extension of the mixing shaft 208 towards the bottom end wall 217. Alternatively, when the actuation mechanism 170 is mounted and/or positioned adjacent to the lower end 32, reducing the stroke length includes reducing the retraction of the mixing shaft 208 towards the bottom end wall 217. In a further embodiment, as the settlement 605 breaks up the actuation mechanism 170 adjusts the stroke length and/or speed until the settlement 605 is dissipated or the full stroke length 607 and/or speed is reached. Additionally, the stroke length and/or speed may be adjusted by the actuation mechanism 170 to reduce or eliminate cell shear in the solution. For example, the stroke length and/or speed may be adjusted to reduce or eliminate the formation of air bubbles as the solution is mixed, which reduces or eliminates damage to cells in the solution from the popping of the air bubbles.

The stroke length and/or speed is adjusted in any suitable manner, such as, but not limited to, continuously (e.g., in response to changes in measurements of the solution), incrementally, according to a pre-programmed protocol and/or schedule, or a combination thereof. For example, in one embodiment, the thickness 608 of the settlement 605 is continuously measured, and the stroke length and/or speed are increased in response to decreases in the thickness 608. The thickness 608 of the settlement 605 is measured by any suitable measurement device 610, such as, but not limited to, an optical interface sensor. The measurement device 610 forms a portion of the tank assembly 10 and/or the mixing assembly 200, is coupled to the actuation mechanism 170, and/or either directly or indirectly provides measurements to the actuation mechanism 170.

In another embodiment, the actuation mechanism 170 adjusts the stroke length and/or speed according to a pre-programmed schedule, such as, but not limited to, a protocol based upon expected dissolution of the settlement 605 and/or inclusion of additional components. The pre-programmed protocol includes providing at least a first stroke length and a first stroke speed for a first duration, and a second stroke length and a second stroke speed for a second duration. Additional stroke lengths and speeds may be provided for additional durations based up solution characteristics such as, but not limited to, volume of the solution, the components in the solution, an amount of the settlement, or a combination thereof. Any suitable combination of stroke lengths, stroke speeds, and/or durations is provided to mix the solution within the mixing bag and or all of which may be varied or held constant with respect to one another. For example, a protocol may include providing a first stroke length of 3 inches for a duration of 5 minutes, followed by a second stroke length of 5 inches for a duration of 10 minutes, while the stroke speed remains constant.

The protocol may be determined based upon a variety of factors, including the size of the tank assembly, the size of the mixing bag, the volume of the solution in the mixing bag, the components in the solution, the thickness of any settlement, solution viscosity, etc. For example, solutions having thicker settlement may include decreased initial stroke length, while solutions having decreased viscosity may have increased stroke speed.

By varying the stroke length with the actuation mechanism 170, the mixing system 10 provides a varied stroke length without adjusting the center of a fixed crank. Additionally, the variable stroke length decreases stress and/or damage to the mixing assembly 200 and/or the actuation mechanism 170 after the settlement 605 has formed. Furthermore, the variable stroke length decreases stress and/or damage to cells that may be present in the solution.

Once the feed component 603 and the fluid component 601 are mixed to form, for example, a homogenous or substantially homogenous solution, the solution is either stored in the mixing bag 202 or dispensed from the compartment 220. Dispensing the solution includes, but is not limited to, dispensing through the delivery tube 420, passing through a filtration system 500, passing through any other tube or system to exit the compartment 220, or a combination thereof. In one embodiment, after dispensing, the mixing bag 202 is refilled, disposed of, or recycled. Refilling the mixing bag 202 may include sterilizing the mixing assembly 200 and/or replacement of one or more components of the mixing assembly 200.

While the invention has been described with reference to one or more embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A mixing method, comprising:
    positioning a mixing assembly in a tank assembly, the mixing assembly including a mixing bag, a mixer disposed within the mixing bag, and a mixing shaft attached to the mixer and extending from the mixing bag;
    dispensing two or more components in a compartment of the mixing bag; and
    mixing the two or more components by repeatedly raising and lowering the mixing shaft a stroke length,
    wherein the stroke length of the mixing shaft is changed during the step of mixing.

2. The method of claim 1, further comprising measuring a quality of at least one of the two or more components in the compartment of the mixing bag and changing the stroke length of the mixing shaft based on changes in the measured quality.

3. The method of claim 2, further comprising using a measurement device to measure the quality of the at least one of the two or more components, the measurement device being in electrical communication with an actuation mechanism that controls movement of the mixing shaft.

4. The method of claim 2, wherein the measured quality comprises a thickness of a settlement of the at least one of the two or more components within the mixing bag.

5. The method of claim 2, further comprising setting an initial stroke length based on the measured quality.

6. The method of claim 2, wherein the quality is measured by an optical sensor.

7. The method of claim 1, further comprising measuring a thickness of a settlement of the at least one of the two or more components within the mixing bag at different times.

8. The method of claim 7, further comprising varying the stroke length in response to changes in the measured thickness of the settlement of the at least one of the two or more components.

9. The method of claim 7, further comprising setting an initial stroke length based on the measured thickness of the settlement of the at least one of the two or more components.

10. The method of claim 9, further comprising increasing the stroke length as the thickness of the measured settlement decreases.

11. The method of claim 1, further comprising changing the stroke length during mixing according to a predetermined schedule.

12. The method of claim 1, further comprising adjusting the speed at which the mixing shaft raises and lowers.

13. The method of claim 1, further comprising attaching the mixing shaft to a linear motor and using the liner motor to raise and lower the mixing shaft.

14. The method of claim 13, wherein the linear motor comprises a servo motor.

15. The method of claim 13, wherein the linear motor is selected from the group consisting of a linear actuator, air cylinders, and combinations thereof.

16. The method of claim 13, wherein the linear motor provides a continuously variable stroke length.

* * * * *